United States Patent [19]

Koehler et al.

[11] Patent Number: 5,008,398

[45] Date of Patent: Apr. 16, 1991

[54] PREPARATION OF P-NITROPHENYL-IMIDAZOLES

[75] Inventors: Hermann Koehler, Bobenheim; Klaus Ebel, Mutterstadt; Helmut Karn, Ludwigshafen; Christof Taubitz, Wachenheim, all of Fed. Rep. of Germany

[73] Assignee: BASF Aktiengesellschaft, Ludwigshafen, Fed. Rep. of Germany

[21] Appl. No.: 416,027

[22] Filed: Oct. 2, 1989

[30] Foreign Application Priority Data

Oct. 15, 1988 [DE] Fed. Rep. of Germany ....... 3835195

[51] Int. Cl.$^5$ .......................................... C07D 233/60
[52] U.S. Cl. .................................................. 548/342
[58] Field of Search ........................................ 548/342

[56] References Cited

PUBLICATIONS

Van Es et al. J. Chem. Soc. 1363–1370 (1963).
Hurso Heterocycles 27, 371–376 (1988).
Japp et al, J. Chem., Soc. 462–472 (1886).
Davidson et al, J. Org. Chem. 2, 319–326 (1938)

*Primary Examiner*—John M. Ford
*Attorney, Agent, or Firm*—John H. Shurtleff

[57] ABSTRACT

A process for the preparation of imidazoles which are substituted with p-nitrophenyl in the 2- and/or 4- and/or 5-position and may carry additional substituents, by reacting imidazoles which are substituted by phenyl in the 2- and/or 4- and/or 5-position and may carry additional substituents with mixtures of sulfuric acid and nitric acid, wherein the reaction is carried out in the presence of urea.

6 Claims, No Drawings

PREPARATION OF P-NITROPHENYL-IMIDAZOLES

The present invention relates to a process for the preparation of p-nitrophenyl-imidazoles.

J. Chem. Soc. 1363-1370 (1963) discloses the preparation of 4,5-bis-(p-nitrophenyl)-imidazole compounds from 4,5-diphenyl-imidazole compounds by means of nitrating acid. However, the yields of 4,5-bis-(p-nitrophenyl)-imidazoles leave something to be desired.

Heterocycles 27, 371-376 (1988) discloses that the nitration of 4(5)-phenylimidazole predominantly leads to the too highly nitrated 4-p-nitrophenyl-5-nitroimidazole, even if nitric acid is employed in stoichiometric amounts. 4(5)-p-Nitrophenyl-imidazole is formed only as a byproduct.

It is an object of the present invention to provide better access to p-nitrophenyl-imidazoles and to remedy the disadvantages of the prior art processes.

We have found that this object is achieved by a process for the preparation of imidazoles which are substituted with p-nitrophenyl in the 2- and/or 4- and/or 5-position and may carry additional substituents, by reacting imidazoles which are substituted by phenyl in the 2- and/or 4- and/or 5-position and may carry additional substituents with mixtures of sulfuric acid and nitric acid, in which process the reaction is carried out in the presence of urea.

Phenylimidazole compounds are known or may be prepared by conventional processes described in the literature, eg. in J. Chem. Soc. 49, 462-472 (1886) or J. Org. Chem. 2, 319-326 (1938).

Preferred phenylimidazoles are those of the general formula II

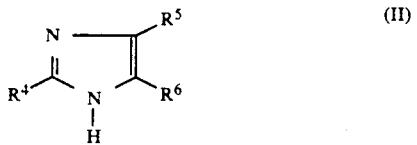

(II)

where $R^4$, $R^5$ and $R^6$ independently of one another are hydrogen, alkyl, cycloalkyl, phenyl or p-nitrophenyl, with the proviso that one or more of the radicals $R^4$, $R^5$ and $R^6$ is phenyl, while the others may be identical or different and may, independently of one another, be hydrogen, linear or branched alkyl of 1 to 18 carbon atoms, cycloalkyl of 5 to 8 carbon atoms, phenyl or p-nitrophenyl.

p-Nitrophenyl-imidazoles of the general formula I

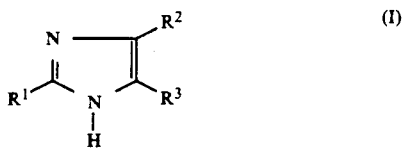

(I)

where $R^1$, $R^2$ and $R^3$ independently of one another are hydrogen, alkyl, cycloalkyl or p-nitrophenyl, with the proviso that one or more of $R^1$, $R^2$ and $R^3$ is p-nitrophenyl, are preferred; the other radicals may be identical or different and may, independently of one another, be hydrogen, linear or branched alkyl of 1 to 18 carbon atoms, cycloalkyl of 5 to 8 carbon atoms or p-nitrophenyl.

Examples of phenylimidazoles of the formula II are 2-phenylimidazole, 4(5)-phenylimidazole, 2-phenyl-4(5)-methylimidazole, 2-methyl-4(5)-phenylimidazole, 2-ethyl-4(5)-phenylimidazole, 4,5-diphenylimidazole, 4(5)-methyl-2,5(4)-diphenylimidazole, 2-methyl-4,5-diphenylimidazole, 2-ethyl-4,5-diphenylimidazole, 2-propyl-4,5-diphenylimidazole, 2-isopropyl-4,5-diphenylimidazole, 2-butyl-4,5-diphenylimidazole, 2-cyclopentyl-4,5-diphenylimidazole, 2-cyclohexyl-4,5-diphenylimidazole, 2,4,5-triphenylimidazole, 2-(p-nitrophenyl)-4,5-diphenylimidazole and 2-phenyl-4,5-bis-(p-nitrophenyl)-imidazole.

Reaction of the phenylimidazoles II with nitric acid/sulfuric acid mixtures gives the corresponding p-nitrophenyl-imidazoles I. Carrying out the reaction in the presence of urea is novel and particularly advantageous.

For this purpose, urea may be employed as a solid or as an aqueous solution containing, for example, from 10 to 60% by weight of urea. In general, the reaction solution contains from 0.02 to 3 mole, preferably from 0.1 to 1 mole, of urea per mole of phenylimidazole II.

The reaction may be carried out batchwise or continuously in apparatus suitable for the purpose. For instance, in batchwise operation the starting material together with the urea may be dissolved in sulfuric acid, and nitric acid subsequently run into this solution.

The nitric acid employed may, for example, be of 35 to 100% strength. Advantageously, technical-grade concentrated nitric acid of from 63 to 68% strength is used.

The nitric acid is employed in at least stoichiometric amounts, for example from 1 to 5 equivalents, preferably from 1 to 1.5 equivalents, per phenyl radical to be nitrated.

Sulfuric acid may be employed as, for example, from 90 to 100% strength acid or as oleum containing up to 65% of sulfur trioxide. The use of technical-grade concentrated sulfuric acid of 96-98% strength is preferred.

The amount of sulfuric acid is not particularly critical. Usually, the amount is so chosen as to give a reaction mixture which can readily be stirred; for example, from 1 to 4 parts by weight per part by weight of phenylimidazole compound II to be nitrated are employed.

The reaction is carried out at from 20° to 220° C., preferably from 40° to 140° C., more especially from 50° to 120° C.

The process according to the invention gives the p-nitrophenyl-imidazole I in very good yield, often of 90% or more.

The p-nitrophenyl-imidazole I is isolated in a conventional manner, for example by diluting the reaction solution with water, neutralizing with a basic compound and filtering off the product. Because of the selective course of the nitration reaction, the product is obtained in high purity, so that further working-up, for example by recrystallization, is in most cases superfluous.

The p-nitrophenyl-imidazoles of the formula I thus obtained are valuable intermediates, for example for the preparation of plastics.

The Examples which follow illustrate the invention without implying any limitation.

EXAMPLE 1

Preparation of 4,5-bis-(4-nitrophenyl)-imidazole 110 g (0.5 mol) of 4,5-diphenylimidazole and 15 g (0.25 mol) of urea were introduced into 250 g of concentrated (98%) sulfuric acid. 110 g of concentrated (63%) nitric acid were then added dropwise at 70°–80° C. and the mixture was stirred for a further 30 minutes at 70° C. When the reaction mixture had cooled, it was poured into 1 liter of ice water and brought to pH 10 with concentrated (25%) ammonia solution. The product which precipitated was filtered off with suction and washed with hot water. 148 g (95.5%) of 4,5-bis-(4-nitrophenyl)-imidazole were obtained, melting point 294°–296°

EXAMPLE 2

Preparation of 2-methyl-4,5-bis-(4-nitrophenyl)-imidazole 117 g (0.5 mol) of 2-methyl-4,5-diphenylimidazole and 15 g (0.25 mol) of urea were introduced into 270 g of concentrated (98%) sulfuric acid. 110 g of concentrated (63%) nitric acid were then added dropwise at 80°–90° C. and the mixture was stirred for a further 2 hours at 80° C. When the reaction mixture had cooled, it was poured into 1 liter of ice water and brought to pH 8 with concentrated (25%) ammonia solution. The product which precipitated was filtered off with suction and washed with hot water. 150 g (92.6%) of 2-methyl-4,5-bis-(4-nitrophenyl)-imidazole were obtained, melting point 230°–232° C.

EXAMPLE 3

Preparation of 2,4,5-tris-(4-nitrophenyl)-imidazole 148 g (0.5 mol) of 2,4,5-triphenylimidazole and 15 g (0.25 mol) of urea were introduced into 440 g of concentrated (98%) sulfuric acid. 220 g of concentrated (63%) nitric acid were then added dropwise at 60°–70° C. and the mixture was stirred for a further 0.5 hour at 60° C. When the reaction mixture had cooled, it was poured into 1.5 liters of ice water and the product which precipitated was filtered off with suction and washed with hot water. 197 g (91.4%) of 2,4,5-tris-(4-nitrophenyl)-imidazole, melting point 320°–322° C., were obtained.

EXAMPLE 4

Preparation of 4(5)-(4-nitrophenyl)-imidazole 72 g (0.5 mol) of 4(5)-phenylimidazole and 15 g (0.25 mol) of urea were introduced into 150 g of concentrated (98%) sulfuric acid. 60 g of concentrated (63%) nitric acid were then added dropwise at 60°–70° C. and the mixture was stirred for a further 1 hour at 60° C. When the reaction mixture had cooled, it was poured into 1 liter of ice water and brought to pH 7 with concentrated (25%) ammonia solution. The product which precipitated was filtered off with suction and washed with hot water. 83 g (87.8%) of 4(5)-(4-nitrophenyl)-imidazole were obtained, melting point 222°–224° C.

We claim:

1. In a process for the preparation of a p-nitrophenyl-imidazole of the formula

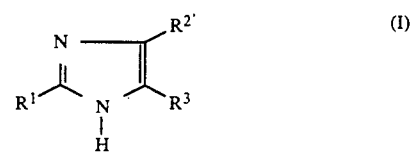

where $R^1$, $R^2$ and $R^3$ independently of one another are hydrogen, alkyl, cycloalkyl or p-nitrophenyl, with the proviso that one or more of the radicals $R^1$, $R^2$ and $R^3$ is p-nitrophenyl, by reacting a phenylimidazole of the formula

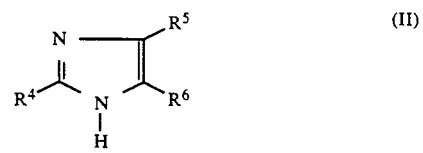

where $R^4$, $R^5$ and $R^6$ independently of one another are hydrogen, alkyl, cycloalkyl, phenyl or p-nitrophenyl, with the proviso that one or more of the radicals $R^4$, $R^5$ and $R^6$ is phenyl, with mixtures of sulfuric acid and nitric acid, the improvement which comprises:

carrying out the reaction in the presence of urea.

2. The process as claimed in claim 1, wherein from 0.02 to 3 moles of urea are used per mole of phenylimidazole.

3. The process as claimed in claim 1, wherein the reaction is carried out at a temperature of from 20° to 220° C.

4. The process as claimed in claim 1, wherein the reaction is carried out at a temperature of from 40° to 140° C.

5. The process as claimed in claim 1, wherein the nitric acid is employed in an amount of from 1 to 5 equivalents per phenyl radical to be nitrated.

6. The process as claimed in claim 1, wherein the nitric acid is employed in an amount of from 1 to 1.5 equivalents per phenyl radical to be nitrated.

* * * * *